United States Patent [19]

Croci et al.

[11] 4,181,656

[45] Jan. 1, 1980

[54] MANUFACTURE OF SEMI-SYNTHETIC PENICILLIN ANTIBIOTICS

[75] Inventors: Marco Croci, Milan; Gino Cotti, Monza, both of Italy

[73] Assignee: Glaxo Group Limited, London, England

[21] Appl. No.: 914,287

[22] Filed: Jun. 9, 1978

Related U.S. Application Data

[63] Continuation of Ser. No. 758,311, Jan. 10, 1977, abandoned.

[30] Foreign Application Priority Data

Jan. 15, 1976 [IT] Italy ............................... 47643 A/76

[51] Int. Cl.$^2$ ........................................... C07D 499/68
[52] U.S. Cl. .................................................. 260/239.1
[58] Field of Search ...................................... 260/239.1

[56] References Cited

FOREIGN PATENT DOCUMENTS 1008468 10/1965 United Kingdom .
1269697  4/1972 United Kingdom .

*Primary Examiner*—Gerald A. Schwartz
*Attorney, Agent, or Firm*—Bacon & Thomas

[57] ABSTRACT

A process for preparing semi-synthetic penicillin antibiotics, especially ampicillin, is disclosed which comprises silylating 6-aminopenicillanic acid using a silylating agent which generates a primary or secondary carboxamide base, and then acylating the silylated 6-aminopenicillanic acid in situ using the primary or secondary carboxamide base as hydrogen halide acceptor. No further base needs to be added, and the products may be obtained in good yield and high purity with the amount of toxic contaminants in the products significantly reduced. Unpleasant side-effects may thus be substantially eliminated.

11 Claims, No Drawings

MANUFACTURE OF SEMI-SYNTHETIC PENICILLIN ANTIBIOTICS

This is a continuation of application Ser. No. 758,311, filed Jan. 10, 1977 now abandoned.

This invention relates to improvements in or relating to the manufacture of semi-synthetic penicillin antibiotics.

Numerous processes have been proposed for preparing the semi-synthetic range of penicillin antibiotics, and particularly ampicillin. These proposals have generally involved the acylation of 6-aminopenicillanic acid (6-APA) or a protected derivative thereof using, for example, an acid halide serving to introduce the desired acyl group. Particularly favoured protected derivatives have been those which may readily by cleaved in situ once the acylation has been effected.

One of the more favoured types of protected derivative of 6-APA have been the mono- or bis- silylated intermediate. Silylated intermediates have been widely used for many years since they have the advantages not only that the silyl groups assist in solubilising the penicillin compounds so that reaction may be performed in aprotic solvents, thus preventing a certain amount of β-lactam hydrolysis, but also that they may readily be cleaved in situ following acylation. British Pat. Nos. 959,853; 964,449 and 1,008,468 for example, describe both the preparation and subsequent use of silylated 6-APA intermediates in penicillin antibiotic production.

The actual acylation step using the silylated intermediate is frequently carried out using an acid halide of the carboxylic acid whose acyl group it is proposed to introduce in the presence of an organic base as hydrogen halide acceptor. The great majority of bases previously employed or proposed to be employed in this role have been amines, particularly secondary or tertiary amines such as trialkylamines, dialkylanilines, piperidines or pyridines. Furthermore such acylations have occasionally been proposed to be carried out in tertiary amide solvents, as in for example, British Pat. No. 959,853.

It has been a disadvantage of such known processes that the acylated antibiotic products obtained tend to be contaminated, even after purification, with minor amounts of the base or solvent employed in their preparation which are extremely difficult to remove from the antibiotic and which frequently possess significant toxicity. It is, of course, desirable that any pharmaceutical product be prepared and sold in the highest degree of purity possible and it is a fact that even the very small amounts of base with which the antibiotic product is contaminated may produce unpleasant side effects when the antibiotics are administered. These include headaches, nausea or drowsiness and it is accordingly highly important either that the amounts of such contaminants in the antibiotic be minimised, or that the contaminants possess lower toxicity.

The disadvantages outlined above have applied particularly to the dialkylanilines when these have been used as bases. The dialkylanilines and especially dimethylaniline, have been extensively used commercially as hydrogen halide acceptors in the acylation reaction since their $pK_b$ values fall within the critical narrow range for the maximisation of yield of antibiotic product and avoidance of side-reactions. Unfortunately they have been found to occlude to a small extent into the antibiotic product and they also possess marked toxicity. The small amounts of, for example, dimethylaniline which occlude into the antibiotic product are sufficient to produce unpleasant side-effects, including those outlined above.

We have now found that if the silylation of the 6-aminopenicillanic acid is carried out using silylating agents which generate primary or secondary carboxamide bases after transfer of the silyl group or groups to the 6-APA molecule, the acylation of the silylated intermediate may be carried out in situ in the presence of the primary or secondary carboxamide bases as hydrogen halide acceptors. Thus, it is a feature of our discovery that no further base needs to be added to the reaction mixture after the silylation and the overall process involves fewer steps and is generally more convenient.

By this method, the good yields of product which have previously been obtained by this type of acylation may be maintained even on a commercial scale, and also the antibiotic product obtained is significantly less contaminated with base than has previously been the case, especially where dimethylaniline has been employed. Our process has the further advantage that the basic contaminants which may be present in the antibiotic products are significantly less toxic than those previously employed, and so the incidence of side effects on administration of the antibiotic may be reduced, if not substantially eliminated.

According to one embodiment of the invention, therefore, there is provided a process for the manufacture of a 6-acylaminopenicillanic acid antibiotic product in which 6-aminopenicillanic acid is reacted in an inert solvent with a silylating agent to form a silylated compound of formula (III)

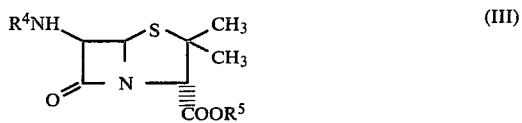

wherein $R^4$ represents a hydrogen atom or a tri($C_{1-6}$) alkylsilyl group or triarylsilyl group and $R^5$ represents a tri($C_{1-6}$) alkylsilyl group or triarylsilyl group, and the compound of formula (III) is thereafter contacted with an acid chloride or protected acid chloride corresponding to the desired 6-acylamino group, the silyl groups are cleaved and the desired antibiotic product is recovered, wherein silylation is effected using a compound of formula (I) or formula (II)

$$R^1R^2N.COR^3 \quad (I)$$

or

$$R^1N=C(OR^2).R^3 \quad (II)$$

wherein $R^1$ is hydrogen or a $C_{1-6}$ alkyl or aralkyl group in formula (I), or a $C_{1-6}$ alkyl or aralkyl or a tri($C_{1-6}$) alkylsilyl or triarylsilyl group in formula (II), $R^2$ is a tri($C_{1-6}$) alkylsilyl or triarylsilyl group and $R^3$ is a $C_{1-6}$ alkyl or aralkyl group or an amino group substituted by one or two $C_{1-6}$ alkyl groups, and the compound of formula (III) produced is reacted without intermediate isolation with the acid chloride or protected acid chloride.

The acid chloride employed is chosen according to the nature of the desired 6-acylamino group. Where the latter contains sensitive groups it may be necessary to protect these during the process of the invention.

Thus, in manufacturing ampicillin, the α-amino group of the D(−)-α-phenylglycyl chloride may be protected by, for example, hydrochloric acid. The process according to the invention is generally applicable to the manufacture of known semi-synthetic penicillin antibiotics, e.g., ampicillin, cloxacillin and dicloxacillin, the nature of which is well defined in existing literature.

It will be appreciated that once the silylating agent of formula (I) or formula (II) has lost its silyl group or groups, a compound of formula (IV)

$$R^3CO.NHR^{1'} \qquad (IV)$$

will be formed wherein $R^3$ is as defined above for formulae (I) and (II) and $R^{1'}$ is a hydrogen atom, $C_{1-6}$ alkyl or aralkyl group. $R^{1'}$ in formula (IV) will, of course represent a hydrogen atom if a silylating agent of formula (II) wherein $R^{1'}$ represents a silyl group is employed.

In view of the nature of the silylating agent used to prepare the compound of formula (III), the compound of formula (IV) as defined above, which is the residue of the silylating agent once silylation has occurred, functions as hydrogen chloride acceptor in the acylation step. It is thus an advantageous feature of the process of the present invention that no further base as hydrogen halide acceptor needs to be added to the reaction solution prior to acylation. Silylating agents which yield compounds of formula (IV) wherein $R^3$ is a lower alkyl (e.g., $C_{1-4}$) group are preferred, and those which yield compounds wherein $R^3$ is a methyl group are especially preferred, for example N-trimethylsilylacetamide, N,O-bis-trimethylsilyl acetamide and N-methyl-N-trimethylsilylacetamide. The silylating agents which yield a compound of formula (IV) wherein $R^3$ is a methyl group and $R^1$ is a hydrogen atom, i.e., acetamide are particularly preferred in view of the non-toxicity of acetamide. Where an aryl group is present in the silylating agent this will desirably be a monocyclic aryl group, for example containing 5 to 6 carbon atoms, e.g., a phenyl group.

The silylation reaction will desirably be carried out by allowing the 6-APA and silylating agent to react, desirably at elevated temperature and in an inert solvent, for sufficient time to allow complete consumption of the silylating agent. This will generally have occurred within about two hours.

The quantity of silylating agent employed will, of course, depend on the number of silylating groups the various silylating agents possess, but it is generally preferred to use from about 1 to 2 equivalents of the silylating agent relative to the quantity of 6-APA to be silylated.

The silylation is conducted in an inert organic solvent, e.g., a halogenated hydrocarbon, aromatic hydrocarbon or an ether, such as benzene, toluene, methylene chloride, ethylene chloride, chloroform or tetrahydrofuran. Methylene chloride is the solvent of choice.

Once silylation has been effected, the solution will, preferably, be cooled to from +10° C. to −30° C. for example +5° to −25°, e.g. +5° to −5° C. prior to addition of the acyl halide. Addition of the halide may be effected portionwise, the temperature being maintained around or below 0° C.

Once all the acyl halide has been added, temperature control is desirably maintained throughout the acylation reaction, which proceeds comparatively rapidly and should normally be complete withiin 30 minutes to 3 hours, e.g., about 2 hours. The extent of the acylation may be monitored by, for example, determining the proportion of residual starting material by thin-layer chromatography.

We generally prefer in the acylation step to employ a stoichiometric amount of acyl halide, e.g., up to 1 equivalent, advantageously 1.0 equivalent, relative to the quantity of silylated 6-APA. The residual compound that remains from the silylation reaction is preferably present in amounts of 1 to 2 equivalents relative to the molar quantity of silylated 6-APA.

After completion of the acylation reaction, for example as evidenced by consumption of all the starting material present, the resulting solution may be treated with a compound containing active hydrogen, e.g., water, acidified or basified water, an alcohol or a phenol, to remove any silyl groups present in the penicillin reaction product. Water is the preferred desilylating agent for this purpose.

The penicillin antibiotic may then be precipitated, e.g., in the case of ampicillin, by adjusting the pH of the diluted reaction mixture to the isoelectric point with a base, or, in the case of cloxacillin and dicloxacillin by formation of a salt thereof in an organic solvent and the precipitate may be recovered and dried by conventional means. Where it is desired to form a salt of the penicillin anitbiotic, this may be achieved by addition of a suitable base for example an alkali metal alkanoate, e.g., sodium 2-ethylhexanoate.

The process according to the invention is particularly applicable to the manufacture of ampicillin, 6-(D-2-amino-2-phenylacetamido)-2,2-dimethylpenam-3-carboxylic acid, either as a hydrate (e.g., the trihydrate) or in anhydrous form. Other semi-synthetic penicillin antibiotics which may be manufactured by the process according to the invention include amoxycillin, cloxacillin, dicloxacillin, α-carboxybenzylpenicillin esters, oxacillin, fluorcloxacillin and metacillin.

The invention will now be more particularly described in the following Examples which should not be construed as limiting the invention.

In the Examples, the nature and purity of the end products were determined by standard techniques, including polarimetry, spectrophotometry, acidimetry and bioassay. A description of the spectrophotometric method used to assay the ampicillin may be found in British Pharmocopoeia, (1973, H.M.S.O.) on page 30; a description of the bioassay technique employed is given in British Pharmacopoeia (1973, H.M.S.O.) on pages 102–104 of the Appendix; and an account of the acidimetric assay used to assay the cloxacillin and dicloxacillin is given in British Pharmacopoeia (1973, H.M.S.O.) on page 81.

The water content was determined by a Karl Fisher analysis for cloxacillin and dicloxacillin, and by this method or by measuring the weight loss on heating to form the anhydrous compound in the case of ampicillin trihydrate.

The purity of the ampicillin products is given after allowance has been made for the water (hydrate) content of the ampicillin product obtained.

In the Examples, the specific rotation of ampicillin trihydrate is determined at c=0.25% solutions in water, and the specific rotations of dicloxacillin and cloxacillin are determined at c=1.0% in water, the determinations being carried out at 20° C.

The specific rotation of anhydrous ampicillin is given as $[\alpha]_D^{20} = +280°$ to $+300°$ (c=0.25 in water) and that of cloxacillin as sodium salt monohydrate is given as $[\alpha]_D^{20} = +156°$ to $+164°$ (c=1 in water) in the British Pharmacopoeia (1973, H.M.S.O.). That of dicloxacillin is given as $[\alpha]_D^{24} = +134°$ (c=0.4 in water) in the Merck Index (8th Edition).

EXAMPLE 1

Preparation of 6 (D-2-amino-2-phenylacetamido)-2,2-dimethylpenam-3-carboxylic acid trihydrate using N-trimethylsilylacetamide as silylating agent 52.5 g (0.400 mols) of N-trimethylsilylacetamide were added to a suspension of 43.2 g (0.200 mols) of 6-APA in 350 ml of methylene chloride under agitation. The mixture was heated to +40° C. for 120 minutes, and then cooled to −25° C.; during the cooling there was an abundant precipitation of acetamide. 43.3 g (0.200 mols) (purity 95.0%) of D(-)-α-phenylglycyl-chloride hydrochloride were then added at −25° C. and the temperature was allowed to increase to −5° C. where it was held for a total period of 90 minutes starting from the addition of the acid chloride hydrochloride. 450 ml of water were added, and then the ampicillin trihydrate was precipitated by adjusting the pH to 4.5 with dilute NH4OH. After sixty minutes agitation at +10° C./+15° C., the mixture was filtered and then washed with 2×75 ml of water and 3×125 ml of acetone; the solid was dried at +35° C./+40° C.

Yield: 84.0±1.0%

Specific rotation: +29.6°±1°, (obtained from a value of +256°±1° for the hydrated compound). Spectrophotometric assay: 99.0±0.5% (obtained from an ampicillin purity of 85.7%±0.5% for the hydrated compound).

Water content: between 13.4 and 14.0%.

EXAMPLE 2

Preparation of 6-(D-2-amino-2-phenylacetamido)-2,2-dimethylpenam-3-carboxylic acid trihydrate using N,O-bis-trimethylsilylacetamide as silylating agent 48.9 ml (0.200 mols) of N,O-bis-trimethyl-silylacetamide were added to a suspension of 43.2 g (0.200 mols) of 6-aminopenicillanic acid in 350 ml of methylene chloride under agitation. The mixture was heated at +40° C. for 120 minutes, then cooled to −25° C. and 43.3 g (0.200 mols); (purity 95.0%) of D(-)-α-phenylglycyl-chloride hydrochloride were added and thereafter the procedure followed was as that described in Example 1.

Yield: 80.0%.

Specific rotation: +296°.

Spectrophotometric assay: 98.7%.

Water content: 13.9%.

EXAMPLE 3

Preparation of 6-[3-(2-chlorophenyl)-5-methyl-4-isoxazolecarboxamido]-2,2-dimethylpenam-3-carboxylate (cloxacillin)sodium monohydrate using N-trimethylsilylacetamide as silylating agent 52.5 g (0.400 mols) of N-trimethylacetamide were added to a suspension of 43.2 g (0.200 mols) of 6-aminopenicillanic acid in 350 ml of methylene chloride under agitation. The mixture was heated at +40° C. for 120 minutes and then cooled to −25° C.; during the cooling acetamide precipitated. 51.2 g (0.200 mols) of 3-(2-chlorophenyl)-5-methylisoxazolyl-4-carbonyl chloride were added; the temperature was allowed to increase to 0° C. and held there for a total period of 60 minutes starting from the addition of the acid chloride. 175 ml of methyl isobutyl ketone and 300 ml of water were then added; the phases were separated and the aqueous phase was discarded; the organic phase was again washed with 300 ml of water, and the aqueous phase discarded. The organic phase was treated for 30 minutes with anhydrous sodium sulphate; the drying agent was then filtered off and washed with 175 ml of methyl isobutyl ketone which was combined with the main organic phase. The sodium salt monohydrate of cloxacillin was then precipitated by adding to the combined organic phases 200 ml of a 1N solution of sodium 2-ethyl hexanoate in methyl isobutyl ketone. After 60 minutes agitation the crystalline white solid was filtered and then washed with 3×150 ml of acetone; drying was in vacuum oven at +35° C./+40° C.

Yield: 84.6%

Acidimetric assay: 98.8% as sodium salt monohydrate.

Specific rotation: +163°.

Water content: 3.9%.

EXAMPLE 4

Preparation of 6-[3-(2,6-dichlorophenyl)-5-methyl-4-isoxazolecarboxamido]-2,2-dimethylpenam-3-carboxylate (dicloxacillin) sodium monohydrate using N-trimethylsilylacetamide as silylating agent 52.5 g (0.400 mols) of N-trimethylsilylacetamide were added to a suspension of 43.2 g (0.200 mols) of 6-aminopenicillanic acid in 350 ml of methylene chloride under agitation. The mixture was heated at +40° C. for 120 minutes, and then cooled to −25° C.; during the cooling, acetamide precipitated. 58.1 g (0.200 mols) of 3-(2,6-dichlorophenyl)-5-methylisoxazolyl-4-carbonylchloride were added at −25° C., and the temperature was allowed to increase to 0° C. where it was held for a total period of 60 minutes starting from the addition of the acid chloride. 175 ml of methyl isobutyl ketone and 300 ml of water were added and the phases separated. The aqueous phase was discarded, the organic phase was again washed with 300 ml of water and the aqueous phase again discarded. The organic phase was treated for 30 minutes with anhydrous sodium sulphate; the drying agent was then filtered, and washed with 175 ml of methyl isobutyl ketone, which was combined with the main organic phase. The sodium salt monohydrate of dicloxacillin was precipitated by adding to the combined organic phases 200 ml of a 1N solution of sodium 2-ethylhexanoate in methyl isobutyl ketone. After 60 minutes' agitation the crystalline white solid was filtered, washed with 3×150 ml of acetone and dried in vacuum oven at +35° C./+40° C.

Yield: 81.8%

Acidimetric assay: 98.6% as sodium salt monohydrate.

Specific rotation: +139°.

Water content: 3.8%.

EXAMPLE 5

Preparation of 6-(D-2-amino-2-phenylacetamido)-2,2-dimethylpenam-3-carboxylic acid trihydrate using N-trimethylsilyl acetamide as silylating agent A mixture of 43.2 g (0.20 mols) of 6-animopenicillanic acid, 350 ml of methylene chloride and 52.5 g (0.40 mols) of N-trimethylsilylacetamide was heated under reflux for two hours. The temperature of the mixture was then lowered to −5° C. and 43.2 g (0.2 mols, purity 95%) of D(-)-α-phenylglycyl chloride hydrochloride were added, the temperature being maintained below 0° C. After stirring for one and a half hours, between 0° C. and +10° C., the temperature was lowered to 0° C. and 450 ml of water added. Ampicillin trihydrate was precipitated by adjusting the pH to 4.5 with diluted $NH_4OH$ and the crystalline product was filtered, washed with water and acetone and then dried.

Yield: 82.7%.
Spectrophotometric assay: 99.0%.
Bioassay: 97.9%.
Specific rotation: +296°.
Water content: 13.4%.

EXAMPLE 6

Preparation of 6-(D-2-amino-2-phenylacetamido)-2,2-dimethylpenam-3-carboxylic acid trihydrate using N-methyl N-trimethylsilylacetamide as silylating agent 58.1 g (0.40 mols) of N-methyl-N-trimethylsilylacetamide were added, with stirring to a suspension of 43.2 g (0.20 mols) of 6-aminopenicillanic acid in 350 ml methylene chloride. The mixture was heated at +40° C. for 120 minutes and then cooled to −25° C. Thereafter, the procedure was as described in Example 1.

A yield of 79.3% was obtained.
Specific rotation: +292°.
Spectrophotometric assay: 97.6%.
Water content: 13.7%.

We claim:

1. In a process for the manufacture of a 6-acylaminopenicillanic acid antibiotic product in which 6-aminopenicillanic acid is reacted in an inert organic solvent with from about 1 to about 2 equivalents of a silylating agent relative to the molar quantity of 6-aminopenicillanic acid to form a silylated compound of formula (III)

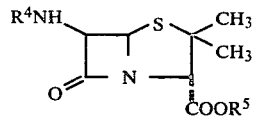

wherein $R^4$ is selected from the group consisting of hydrogen, tri($C_{1-6}$)alkylsilyl and tri($C_{5-12}$)arylsilyl and $R_5$ is selected from the group consisting of tri($C_{1-6}$)alkylsilyl and tri($C_{5-12}$)arylsilyl, and the compound of formula (III) is thereafter contacted with an acid chloride or protected acid chloride corresponding to the desired 6-acylamino group at a temperature of from about +10° to about −30° C., the silyl groups are cleaved with water and the desired antibiotic product is recovered, the improvement wherein silylation is effected using a compound selected from the group consisting of formula (I) and formula (II)

and

wherein $R^1$ is selected from the group consisting of hydrogen, $C_{1-6}$ alkyl and $C_{7-20}$ aralkyl in formula (I) or $C_{1-6}$ alkyl, $C_{7-20}$ aralkyl, tri($C_{1-6}$)alkylsilyl and tri($C_{5-12}$)arylsilyl group in formula (II), $R^2$ is selected from the group consisting of tri($C_{1-6}$)alkylsilyl and tri($C_{5-12}$)arylsilyl and $R^3$ is selected from the group consisting of $C_{1-6}$ alkyl, $C_{7-20}$ aralkyl and an amino group substituted by one or two $C_{1-6}$ alkyl groups, and the compound of formula (III) produced is reacted without intermediate isolation and without addition of an additional acid acceptor with the acid chloride or protected acid chloride.

2. The process of claim 1 wherein the silylating agent provides, after silylation, a compound of formula (IV)

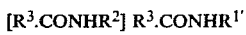

wherein $R^3$ is as defined in claim 1 and $[R^1]$ $R^{1'}$ is hydrogen or $C_{1-6}$ alkyl.

3. The process of claim 2 wherein the compound of formula (IV) is acetamide.

4. The process of claim 1 wherein the silylating agent is N-trimethylsilyacetamide or N,O-bis-trimethylsilyacetamide.

5. The process of claim 1 wherein the protected acid chloride is D-(−)-phenylglycyl chloride hydrochloride.

6. The process of claim 1 wherein the acid chloride is 3-(2,6-dichlorophenyl)-5-methylisoxazolyl-4-carbonyl chloride.

7. The process of claim 1 wherein the acid chloride is 3-(2-chlorophenyl)-5-methylisoxazolyl-4-carbonyl chloride.

8. In a process for the manufacture of ampicillin or a salt or hydrate thereof in which 6-aminopenicillanic acid is reacted in an inert organic solvent with from about 1 to about 2 equivalents of a silylating agent relative to the molar quantity of 6-aminopenicillanic acid to form a silylated compound of formula (III)

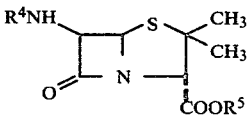

wherein $R^4$ is selected from the group consisting of hydrogen and trimethylsilyl and $R^5$ represents a trimethylsilyl group and the compound of formula (III) is thereafter contacted with D- (−)-phenylglycyl chloride hydrochloride at a temperature of from about +10° to about −30° C., the silyl groups are cleaved with water and the cleaved ampicillin product is recovered, the improvement wherein the silylation is effected using a compound selected from the group consisting of N-trimethylsilylacetamide and N,O-bistrimethylsilylacetamide and the compound of formula (III) produced is reacted, without intermediate isolation and without addition of an additional acid acceptor with the D-(−)-phenylglycyl chloride hydrochloride.

9. The process of claim 8 wherein the antibiotic product recovered is ampicillin trihydrate.

10. In the process as defined in claim 1 for the manufacture of a 6-acylaminopenicillanic acid antibiotic product in which 6-aminopenicillanic acid is reacted in an inert organic solvent with from about 1 to about 2 equivalents of a silylating agent relative to the molar quantity of 6-aminopenicillanic acid to form a silylated compound of formula (III)

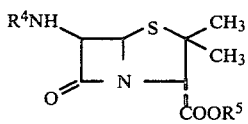

wherein $R^4$ is selected from the group consisting of hydrogen, tri($C_{1-6}$)alkylsilyl and tri($C_{5-12}$)arylsilyl and $R^5$ is selected from the group consisting of tri($C_{1-6}$)alkylsilyl and tri($C_{5-12}$)arylsilyl, and the compound of formula (III) is thereafter acylated with an acid chloride or protected acid chloride corresponding to the desired 6-acylamino group at a temperature of from about $+10°$ to about $-30°$ C., and the silyl groups are cleaved with water and the resulting 6-acylamino penicillanic acid antibiotic product is recovered, the improvement which comprises silylating the 6-aminopenicillanic acid by reacting it with a silylating compound selected from the group consisting of compounds of formula (I) and formula (II)

$$R^1R^2N.COR^3 \quad (I)$$
and
$$R^1N=C(OR^2).R^3 \quad (II)$$

wherein $R^1$ is selected from the group consisting of hydrogen, $C_{1-6}$ alkyl and $C_{7-20}$ aralkyl in formula (I) or $C_{1-6}$ alkyl, $C_{7-20}$ aralkyl, tri($C_{1-6}$)alkylsilyl and tri($C_{5-12}$)arylsilyl group in formula (II), $R^2$ is selected from the group consisting of tri($C_{1-6}$)alkylsilyl and tri($C_{5-12}$)arylsilyl and $R^3$ is selected from the group consisting of $C_{1-6}$ alkyl, $C_{7-20}$ aralkyl and an amino group substituted by one or two $C_{1-6}$ alkyl groups to obtain a reaction mixture comprising the compound of formula (III) and an amide of formula (IV)

$$R^3CONHR^{1'} \quad (IV)$$

wherein $R^3$ is as defined in formula (III) and $R^{1'}$ is hydrogen, $C_{1-6}$ alkyl or $C_{7-20}$ aralkyl, the amide of formula (IV) or a mixture of the amide of formula (IV) and an excess of the silylating compound being a sole acid acceptor present in the reaction mixture, and acylating the compound of formula (III) by reacting the reaction mixture with the acid chloride or protected acid chloride without intermediate isolation of the compound of formula (III) and without addition of an additional acid acceptor.

11. In the process as defined in claim 8 for the manufacture of ampicillin or a salt or hydrate thereof in which 6-aminopenicillanic acid is reacted in an inert organic solvent with from about 1 to about 2 equivalents of a silylating agent relative to the molar quantity of 6-aminopenicillanic acid to form a silylated compound of the formula (III)

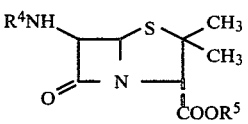

wherein $R^4$ is selected from the group consisting of hydrogen and trimethylsilyl and $R^5$ represents a trimethylsilyl group and the compound of formula (III) is thereafter acylated with D-(−)-phenylglycyl chloride hydrochloride at a temperature of from about $+10°$ to about $-30°$ C., the silyl groups are cleaved with water and the cleaved ampicillin product is recovered, the improvement which comprises silylating the 6-aminopenicillanic acid by reacting it with a silylating compound selected from the group consisting of N-trimethylsilyl acetamide and N,O-bistrimethylsilylacetamide to obtain a reaction mixture comprising the compound of formula (III) and acetamide, acetamide or a mixture of acetamide and an excess of the silylating compound being a sole acid acceptor present in the reaction mixture; and acylating the compound of formula (III) by reacting the reaction mixture with the D-(−)-phenylglycyl chloride hydrochloride, without intermediate isolation of the compound of formula (III) and without adding an additional acid acceptor.

* * * * *